United States Patent [19]
Golubev et al.

[11] Patent Number: 5,837,262
[45] Date of Patent: *Nov. 17, 1998

[54] PHARMACEUTICAL COMPOSITIONS AGAINST SEVERAL HERPES VIRUS INFECTIONS AND/OR ATHEROSCLEROTIC PLAQUE

[75] Inventors: Daniel Golubev, Jackson Heights, N.Y.; Alexander Chaihorsky, Sparks, Nev.

[73] Assignee: Bio-Virus Research Incorporated, Sparks, Nev.

[ * ] Notice: The term of this patent shall not extend beyond the expiration date of Pat. No. 5,534,258.

[21] Appl. No.: 618,917

[22] Filed: Mar. 20, 1996

Related U.S. Application Data

[63] Continuation-in-part of Ser. No. 281,702, Jul. 27, 1994, Pat. No. 5,534,258.

[51] Int. Cl.⁶ .......................... A61K 39/245; A61K 38/00; A61K 39/295; A61K 39/25
[52] U.S. Cl. ....................... 424/231.1; 424/229.1; 424/230.1; 424/202.1; 424/199.1; 424/186.1; 424/188.1; 530/300; 530/324; 530/350; 514/12; 514/824
[58] Field of Search ............................ 424/231.1, 229.1, 424/230.1, 202.1, 199.1, 186.1, 188.1; 530/300, 324, 350; 514/824, 12

[56] References Cited

U.S. PATENT DOCUMENTS

| | | |
|---|---|---|
| 4,322,404 | 3/1982 | Gauri et al. . |
| 4,693,981 | 9/1987 | Wiesehahn et al. . |
| 5,534,258 | 7/1996 | Golubev et al. . |

OTHER PUBLICATIONS

Hajjar 1987, J. Clin. Invest. 80:1317–1321.
Vercelotti 1995, Trends Cardiovasc. Med. 5(4):128–133.
Melnick et al, 1992, Israil J. Med. Sci. 28:463–465.
Hajjar 1991, Am. J. Pathology, 139(6):1195–1211.
Fabricant et al, 1983, Federatin Proc. 42:2476–79.
Pyrzak et al 1987, Atherosclerosis, 68:77–85.
Hajjar 1986, JBC, 261(17):7611–7614.
Lerner et al, Ed:Dixon et al in: Biol of Immunol. Dis. pp. 331–338.
Fabricant et al, 1981, FASEB Mtg. p. 335, Abs. #583.
Melnick et al, 1990, JAMA, 263(16):2204–2207.
Hendrix et al, 1989, Am. J. Pathology, 134(5):1151–1157.
Fabricant et al, 1978, J. Exp. Med. 148:335–340.
Benditt et al, 1983, PNAS, 80:6386–6389.
Homology of Herpesvirus and Human Genes is Probably Involved in the Formation of Atherosclerotic Plaques (ASP), A. Perevozchicov et al; (abstract) presented at the IXth International Congress of Virology, 8 to 13 Aug. 1993, Glasgow, Scotland.
Nieto et al, New Eng. J. Med. 335(9):922–977, Aug. 1996.
Zhou et al, New Eng. J. Med. 335(9):624–630, Aug. 1996.

*Primary Examiner*—Nita Minnifield
*Attorney, Agent, or Firm*—Herbert Dubno; Jonathan Myers

[57] ABSTRACT

A pharmaceutical composition is disclosed for the treatment against several herpes virus infections or atherosclerotic plaques in a mammalian subject suspectible thereto which comprises: (a) 10 to 30% by weight of the peptide of SEQ ID 2; (b) 10 to 30% by weight of the peptide of SEQ ID 4; 10 to 30% by weight of the peptide of SEQ ID 6; and (d) 10 to 30% by weight of the peptide of SEQ ID 8; in combination with a pharmaceutically acceptable inert carrier.

3 Claims, 11 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..84

( x i ) SEQUENCE DESCRIPTION: SEQ ID NO:1:

```
GCC  CCC  CTC  CCC  GCG  CCC  GCG  CCC  CCC  TCC  ACG  CCC  CCG  GGG  CCC  GAG      48
Ala  Pro  Leu  Pro  Ala  Pro  Ala  Pro  Pro  Ser  Thr  Pro  Pro  Gly  Pro  Glu
 1                   5                             10                      15

CCC  GCC  CCC  GCC  CAG  CCC  GCG  GCG  CCC  CGG  GCC  GCC                          84
Pro  Ala  Pro  Ala  Gln  Pro  Ala  Ala  Pro  Arg  Ala  Ala
               20                        25
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala  Pro  Leu  Pro  Ala  Pro  Ala  Pro  Pro  Ser  Thr  Pro  Pro  Gly  Pro  Glu
 1                   5                             10                      15

Pro  Ala  Pro  Ala  Gln  Pro  Ala  Ala  Pro  Arg  Ala  Ala
               20                        25
```

( 2 ) INFORMATION FOR SEQ ID NO:3:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (i v) ANTI-SENSE: NO (i x) FEATURE:
  (A) NAME/KEY: CDS
  (B) LOCATION: 1..75

(x i) SEQUENCE DESCRIPTION: SEQ ID NO:3:

```
GCT  CCT  CCA  GAG  GCC  GAC  GCG  CGG  ACC  CTC  CGA  CGT  CCT  GGC  CCG  CCG      48
Ala  Pro  Pro  Glu  Ala  Asp  Ala  Arg  Thr  Leu  Arg  Arg  Pro  Gly  Pro  Pro
          30                       35                      40

CTG  CCG  CTG  CCG  CCT  TCC  CTT  CTC  CCG                                         75
Leu  Pro  Leu  Pro  Pro  Ser  Leu  Leu  Pro
 45                       50
```

(2) INFORMATION FOR SEQ ID NO:4:

(i) SEQUENCE CHARACTERISTICS:
    (A) LENGTH: 25 amino acids
    (B) TYPE: amino acid
    (D) TOPOLOGY: linear (i i) MOLECULE TYPE: protein (x i) SEQUENCE DESCRIPTION: SEQ ID NO:4:

```
Ala  Pro  Pro  Glu  Ala  Asp  Ala  Arg  Thr  Leu  Arg  Arg  Pro  Gly  Pro  Pro
 1                    5                      10                      15

Leu  Pro  Leu  Pro  Pro  Ser  Leu  Leu  Pro
          20                       25
```

(2) INFORMATION FOR SEQ ID NO:5:

(i) SEQUENCE CHARACTERISTICS:
    (A) LENGTH: 78 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (i x) FEATURE:
    (A) NAME/KEY: CDS
    (B) LOCATION: 1..78

(x i) SEQUENCE DESCRIPTION: SEQ ID NO:5:

```
GGC  ACC  GAC  GGC  CCC  GCC  CGA  GGA  GGC  GGA  AGC  GGA  GGA  GGA  CGC  GGC      48
Gly  Thr  Asp  Gly  Pro  Ala  Arg  Gly  Gly  Gly  Ser  Gly  Gly  Gly  Arg  Gly
                    30                       35                      40

CCC  GGT  GGC  GGA  AGA  GGT  GGC  CCC  CGC  GGG                                    78
Pro  Gly  Gly  Gly  Arg  Gly  Gly  Pro  Arg  Gly
           45                       50
```

(2) INFORMATION FOR SEQ ID NO:6:

(i) SEQUENCE CHARACTERISTICS:
    (A) LENGTH: 26 amino acids
    (B) TYPE: amino acid
    (D) TOPOLOGY: linear (i i) MOLECULE TYPE: protein (x i) SEQUENCE DESCRIPTION: SEQ ID NO:6:

```
Gly  Thr  Asp  Gly  Pro  Ala  Arg  Gly  Gly  Gly  Ser  Gly  Gly  Gly  Arg  Gly
 1                    5                       10                      15

Pro  Gly  Gly  Gly  Arg  Gly  Gly  Pro  Arg  Gly
           20                       25
```

( 2 ) INFORMATION FOR SEQ ID NO:7:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..84

( x i ) SEQUENCE DESCRIPTION: SEQ ID NO:7:

```
GGC  TGG  GCT  GCG  CGG  CGG  GGC  CGG  CGA  CGG  GGA  CGG  CGG  CGG  GGA  CGA      48
Gly  Trp  Ala  Ala  Arg  Arg  Gly  Arg  Arg  Arg  Gly  Arg  Arg  Arg  Gly  Arg
               30                      35                      40

CGT  CGC  CGC  CAG  CGG  CGA  GCG  GCA  CGG  AGA  CGG  AGG                          84
Arg  Arg  Arg  Gln  Arg  Arg  Ala  Ala  Arg  Arg  Arg  Arg
          45                      50
```

( 2 ) INFORMATION FOR SEQ ID NO:8:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Gly  Trp  Ala  Ala  Arg  Arg  Gly  Arg  Arg  Arg  Gly  Arg  Arg  Arg  Gly  Arg
 1              5                      10                     15

Arg  Arg  Arg  Gln  Arg  Arg  Ala  Ala  Arg  Arg  Arg  Arg
          20                      25
```

PHARMACEUTICAL COMPOSITIONS AGAINST SEVERAL HERPES VIRUS INFECTIONS AND/OR ATHEROSCLEROTIC PLAQUE

CROSS REFERENCE TO RELATED APPLICATIONS

This application is a continuation-in-part of Ser. No. 08/281,702 filed 27 Jul., 1994 now U.S. Pat. No. 5,534,258, issued Jul. 8, 1996.

FIELD OF THE INVENTION

This invention relates to a vaccine against herpes virus for treatment and prevention of the development of several herpes virus infections and/or atherosclerotic plaques. More particularly the invention relates to a herpes vaccine containing peptides encoded by parts of herpes virus DNA with homology to alpha-subunits of human G proteins and that acts as a prophylaxis against pathogenic development of several herpes infections and/or atherosclerotic plaque in a mammalian subjected susceptible thereto.

BACKGROUND OF THE INVENTION

It is generally accepted that atherogenesis is triggered by primary injury to the endothelial lining of the arterial walls. This injury is believed to be the result of exposure of the underlying smooth muscle cells to several factors of non-infectious origin (hormones, low density lipoproteins, growth factors, among others). The prevailing view is that human atherosclerosis (AS) is a pleiotropic process with various causes. See Ross, R., The Pathogenesis of Atherosclerosis: An Update, New England J. Med.,314, 488 to 500 (1986).

A fundamentally new etiological factor: herpes virus infection was reported by Fabricant et al, who demonstrated that chickens infected with Marek Disease Virus (MDV) have an unusually high incidence of atherosclerotic plaque (ASP) in the arteries. See Fabricant, C. G. et al, Virus-Induced Cholesterol Crystals, *Science*, 181, 566 to 567 (1973); and Fabricant, C. G. et al, Virus-Induced Atherosclerosis,*J. ExP. Med.*, 148, 335 to 340 (1978). Since that time data have been accumulated suggesting herpes virus in AS in humans. It was shown that different herpes viruses can alter smooth muscle cells lipid metabolism and induce cholesterol and cholesterol ester accumulation in these cells. See Fabricant, C. G. et al, Herpes Virus Infection Enhances Cholesterol and Cholesterol Ester Accumulation in Cultured Arterial Smooth Muscle Cells, *Am. J. Pathol*, 105, 176 to 184 (1981); Fabricant, C. G. et al, Herpes Virus-Induced Atherosclerosis in Chickens, *Fed. Proc.*, 42, 2476 to 2479 (1983); Melnick, J. L. et al, Cytomegalovirus Antigen within Human Arterial Smooth Muscle Cells, *Lancet*, ii, 644 to 647 (1983); Gyorkey, F. et al, Herpesviridae in the Endothelial and Smooth Muscle Cells of Proximal Aorta in Atherosclerotic Patients, *Exp. Mol. Pathol*, 40, 328 to 339 (1984); Hajjar et al, Virus-Induced Atherosclerosis: Herpes Virus Infection Alters Aortic Cholesterol Metabolism and Accumulation,*Am. J. Pathol.*, 122, 62 to 70 (1986); Adam et al, High Levels of Cytomegalovirus Antibody in Patients Requiring Vascular Surgery for Atherosclerosis, *Lancet*, 2, 291 to 293 (1987); Petrie, Association of Herpesvirus/Cytomegalovirus Infections with Human Atherosclerosis, *Prog. Med. Virol.*, 35, 21 to 42 (1988); Grattan, M.T. et al, Cytomegalovirus Infection is Associated with Cardiac Allograft Rejection and Atherosclerosis, *J. A. Med. Assoc.*, 261, 3561 to 3566 (1989); Mc Donald, K. et al, Association of Coronary Artery Disease in Cardiac Transplant Recipients with Cytomegalovirus Infection, *Am. J. Cardiol.*, 64, 359 to 362 (1989); Visser et al, Granulocyte-Mediated Injury in Herpes Simplex Virus-Infected Human Endothelium, *Lab. Invest.*, 60, 296 to 304 (1989); Melnick, J. L. et al, Possible Role of Cytomegalovirus in Atherogenesis, *J. Am. Assoc.*, 263, 2204 to 2207 (1990); Bruggeman, C. A. et al, The Possible Role of Cytomegalovirus in Atherogenesis, *Prog. Med. Virol.*, 38, 1 to 26 (1991); Melnick, J. L. et al, Accelerated Graft Atherosclerosis Following Cardiac Transplantation; Do Viruses Play a Role?, *Clin. Cardiol.*, 14 (Supp. II), 21 to 26 (1991); and Hajjar , D. P., Viral Pathogenesis of Atherosclerosis, *Am. J. Pathol.*, 133, 1195 to 1211 (1991).

In addition the DNA of various herpesviruses showed positive hybridization with ASP DNA; see Benditt, E. P. et al, Viruses in the Etiology of Atherosclerosis, *Proc. Natl. Acad. Sci.*, 80, 6386 to 6389 (1983); Pyrzak, R. et al, Detection of Specific DNA Segments of Marek's Disease Herpes Virus in Japanese Quail Susceptible to Atherosclerosis,*Atherosclerosis*, 68, 77 to 85 (1987); Petrie, B. L. et al, Nucleic Acid Sequences of Cytomegalovirus in Cultured Human Arterial Tissue,*J. Inf. Dis.*, 155, 158 to 159 (1987); Yamashiroya, H. M. et al, Herpesviridae in Coronary Arteries and Aorta of Young Trauma Victims,*Am. J. Pathol*, 130, 71 to 79 (1988); and Hendrix, M. G. R. et al, The Presence of Cytomegalovirus Nucleic Acids in Arterial Walls of Patients Suffering From Grade III Atherosclerosis, *Am. J. Pathol.*, 134, 1151 to 1157 (1989).

No systematic attempts to demonstrate a viral presence in ASP by direct isolation of infectious HSV from ASP and by detection of viral replication in ASP by Electron Microscopy have been reported. A viral presence in ASP would explain the presence of HSV-like DNA in ASP, and redirect research to determine the molecular mechanisms of viral involvement in etiology of atherosclerosis. In such a case, the possibility of a contamination of ASP in the blood vessels by HSV also has to be excluded.

None of the above references deals with the preparation of a vaccine against any form of the herpes virus. The following reference deals with the preparation of a herpes vaccine against Marek's Disease Herpes-Virus in chickens: Fabricant, J. et al, Vaccination Prevents Atherosclerosis Induced by Marek's disease Herpesvirus, College of Veterinary Medicine and Medicine, Cornell University, Ithaca and New York, N.Y. The reference appeared as an abstract in the Federation of American Societies for Experimental Biology, 65th Annual Meeting, Atlanta (1981).

The vaccine employed against Marek's Disease Herpesvirus in chickens was derived from Turkey herpesvirus (HVT). There is no indication that a vaccine against atherosclerosis caused by human herpes virus could be prepared. There is certainly no suggestion to employ a herpes vaccine containing homologous peptide sequences to those of the viral DNA found in strains of the herpes virus that effect humans.

U.S. Pat. No. 4,038,381 discloses a vaccine for the prevention and treatment of vascular conditions, comprising a combination of a tuberculosis antigen with an antiherpetic vaccine. There is no suggestion to employ the four polypeptides of the present invention as the active ingredients in the vaccine. The reference also states that the individual tuberculosis antigen and antiherpetic vaccine had no known per se ability in the prevention or treatment of vascular disease.

OBJECT OF THE INVENTION

It is the object of the invention to provide a universal vaccine as a prophylaxis against pathogenic development of several herpes infections and/or atherosclerotic plaque in a mammalian subject susceptible thereto.

SUMMARY OF THE INVENTION

We have found such a vaccine that is effective as a prophylaxis against pathogenic development of several herpes infections and/or atherosclerotic plaque in mammalian subjects, including humans. The vaccine contains four new peptides as described herein below in the indicated proportions:

(a) 10 to 30% by weight of the compound

Ala Pro Leu Pro Ala Pro Ala Pro Pro Ser Thr Pro Pro Gly Pro Glu
1           5                   10                  15
Pro Ala Pro Ala Gln Pro Ala Ala Pro Arg Ala Ala (Seq ID 2);
            20                  25

(b) 10 to 30% by weight of the compound

Ala Pro Pro Glu Ala Asp Ala Arg Thr Leu Arg Arg Pro Gly Pro Pro
1           5                   10                  15
Leu Pro Leu Pro Pro Ser Leu Leu Pro (Seq ID 4);
            20              25

(c) 10 to 30% by weight of the compound

Gly Thr Asp Gly Pro Ala Arg Gly Gly Gly Ser Gly Gly Gly Arg Gly
1           5                   10                  15
Pro Gly Gly Gly Arg Gly Gly Pro Arg Gly (Seq ID 6); and
            20                  25

(d) 10 to 30% by weight of the compound

Gly Trp Ala Ala Arg Arg Gly Arg Arg Arg Gly Arg Arg Arg Gly Arg
1           5                   10                  15
Arg Arg Arg Gln Arg Arg Ala Ala Arg Arg Arg (Seq ID 8);
            20                  25 in combination with a pharmaceutically acceptable inert vaccine carrier such as normal saline or a physiological oil (e.g. corn oil, sunflower oil).

Preferably each of the four polypeptides is present in the compositions in equal proportions by weight: that is the compositions preferably contain 25% of each of the four polypeptides.

The compositions are prepared by incorporating each of the four polypeptides in the pharmaceutically acceptable inert vaccine carrier such as normal saline or a physiological oil in an adequate concentration of said polypeptides. Preferably there is present 1.0 to 100 µg of each polypeptide per ml of pharmaceutical composition. More preferably one dose of vaccine (1 ml) contains equal parts (20 µg) of each of the 4 polypeptides. Thus the preferred total amount of polypeptides in one dose of vaccine is 80 µg.

Since each of the polypeptides is itself a new compound, each of them, individually, as well as collectively, is considered to be part of the invention as well.

Also contemplated to be within the scope of the invention is a method of prophylaxis of pathogenic development of several herpes virus infections and/or atherosclerotic plaques in a mammalian subject susceptible thereto which comprises the step of administering to said mammalian subject, a therapeutically effective amount of the pharmaceutical composition containing the four polypeptide sequences as described hereinabove. The herpes infections whose development can be prevented include Herpes Simplex I, Herpes Simplex II, Cytomegalovins, Epstein-Barr Virus, Herpes Zoster and Kaposi's Sarcoma.

The compositions may preferably be administered to a mammalian subject parenterally, such as by injection. More preferably the compositions are administered by subcutaneous, intramuscular, intra-arterial, intravenous or intradermal injection. A preferred dosage of the compositions is 1 ml every 20 days administered in a series of 6 intramuscular injections. The full cycle of treatment may consist of 2 or 3 such courses with 3 month intervals in between.

Use of an adjuvant, for instance inorganic gels such as alum, aluminum hydroxide or aluminum phosphate that increase antigenic response, is optional in the compositions.

BRIEF DESCRIPTION OF THE DRAWINGS

The above and other objects, features and advantages will become more readily apparent from the following description, reference being made to the accompanying drawings in which.

Lane a "DNA-GGC-sites-fragment" (25,000 cpm, 2.5 ng of DNA) in the absence of added protein extract and any sera; Lanes b through e: "DNA-GGC-sites-fragments" in the same concentration+aliquot of the extracts of purified nuclei from human blood vessel endothelium cells with ASP (b,c) +aliquot of the normal (pre-immune) rabbit sera N76(d) and N77(e) in dilution 1:2.

Lanes f and g: "DNA-GGC-sites-fragments" in the same concentration+aliquot of the extracts of purified nuclei from human blood vessel endothelium cells without ASP.

Lane h: "DNA-GGC-sites-fragments" in the same concentration+mixture of aliquots of the extract of purified nuclei from endothelial blood vessel cells with ASP+aliquot of the mixture of the post-immune rabbit sera N76 and N77 in dilution 1:100.

Lanes i through 1: the same situation as in Lane "h", but the mixtures of immune sera were used in a decreased dilution of 1:50(i), 1:30(j), 1:20(k), and 1:10(1).

Figure 11:
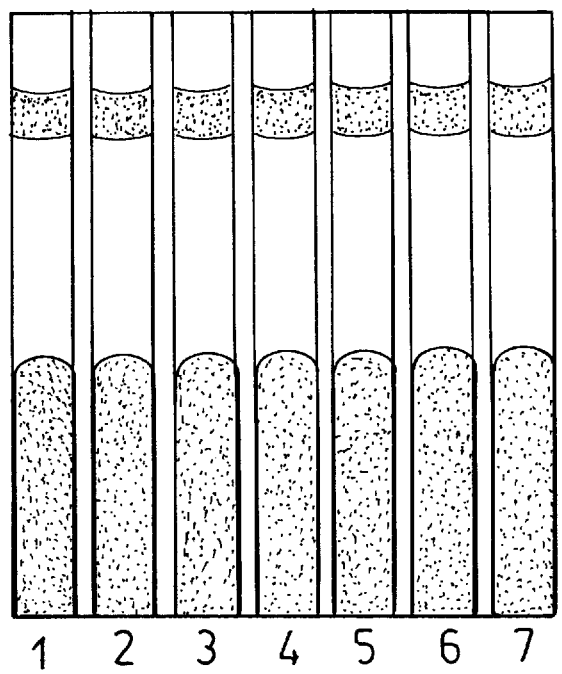

FIG. 11 shows the results of another technique of gel retardation experiments in 5% PAAG. The immunosera number 77(N4) and Number 76(N6) (with dilution 1:20) had decreased the formation (amount of DNA protein complex between DNA-GGC-fragment labelled by $_{32}$P and alpha-protein nuclei from human blood vessels with ASP—in comparison with corresponding preimmune sera (N5 and N7). On the other side both of immune sera (N1) and (N2), as well as the preimmune sera number 76(N3) had no influence on the formation of such complexes, if sera were used in dilution of 1:100

Preparation of the Vaccine against Atherosclerosis

The vaccine may be prepared by recombinant DNA techniques by chemical synthesis or by automated solid phase synthesis. When preparing the vaccine by recombinant DNA techniques the following steps are employed:

Recombinant DNA Synthesis

1. Accumulation of Virus Particles

For isolation of the fragments of DNA that encode peptides having Seq ID 2 and Seq ID 6, it is necessary to accumulate Herpes Simplex Virus Type 1, and for isolation of the fragments of DNA that encode peptides having Seq ID 4 and Seq ID 8, it is necessary to accumulate Human Cytomegalovirus.

Herpes Simplex Virus 1 and Human Cytomegalovirus are each cultivated in diploid human embryonic lung cells (HECL).

Tissue Cultures

For isolation of Herpes Simplex Virus 1 and Human Cytomegalovirus, it is necessary to use diploid human embryonic lung cells (e.g. semi-continuous cells). These cells are derived from embryonic lung tissue and following initial dispersal, they can be redispersed and regrown many times (30 to 50 times). Human embryonic lung tissue, which can be obtained from embryos of 10 to 12 weeks, provide a most valuable source for harvesting a number of different herpes viruses, including Herpes Simplex Viruses and Human Cytomegalovirus.

Semi-continuous cells have a normal chromosome count (diploid) and show the phenomenon of contact inhibition. An inoculum of each virus listed above is placed on the monolayer and allowed to absorb for 1 hour. It is then removed and fresh medium is added. Cultures are incubated at 37° C. and they are inspected regularly by microscopy for evidence of virus growth. The culture medium is normally changed on the day after inoculation to minimize the effect of toxins that may persist in the inoculum, and is then replaced periodically to replenish the supply of nutrients for the cells. Cultures are incubated for various lengths of time depending on the virus. While the cytopathic effects of a concentrated inoculum of herpes virus may appear overnight, a low level of cytomegalovirus may take 3 to 4 weeks to appear.

The cells infected by herpes viruses may be cultivated in suspension also.

For inoculation of the t issue cultures to prepare the peptide vaccines, the following viruses may be used:

Herpes Simplex Type 1 (Human herpesvirus 1, Herpesvirus homines type 1) ATCC VR-539, Strain MacIntyre.

Cytomegalovirus ATCC VR-538 Strain: AD-169.

2. Isolation of the following four nucleotide Sequences from the Viral DNA that Code for the Four peptides indicated above:

```
GCC CCC CTC CCC GCG CCC GCG CCC CCC TCC ACG CCC CCG GGG CCC GAG  48
Ala Pro Leu Pro Ala Pro Ala Pro Pro Ser Thr Pro Pro Gly Pro Glu
1               5                   10                  15
CCC GCC CCC GCC CAG CCC GCG GCG CCC CGG GCC GCC  84  (Seq ID 1);
Pro Ala Pro Ala Gln Pro Ala Ala Pro Arg Ala Ala
                20                  25

GCT CCT CCA GAC GCC GAC GCG CGG ACC CTC CGA CGT CCT GGC CCG CCG  48
Ala Pro Pro Glu Ala Asp Ala Arg Thr Leu Arg Arg Pro Gly Pro Pro
1               5                   10                  15
CTG CCG CTG CCG CCT TCC CTT CTC CCG  75  (Seq ID 3);
Leu Pro Leu Pro Pro Ser Leu Leu Pro
                20                  25

GGC ACC GAC GGC CCC GCC CGA GGA GGC GGA AGC GGA GGA GGA CGC GGC  48
Gly Thr Asp Gly Pro Ala Arg Gly Gly Gly Ser Gly Gly Gly Arg Gly
1               5                   10                  15
CCC GGT GGC GGA AGA GGT GGC CCC CGC GGG  78  (Seq ID 5); and
Pro Gly Gly Gly Arg Gly Gly Pro Arg Gly
                20                  25

GGC TGG GCT GCG CGG CGG GGC CGG CGA CGG GGA CGG CGG CGG GGA CGA  48
Gly Trp Ala Ala Arg Arg Gly Arg Arg Arg Gly Arg Arg Arg Gly Arg
1               5                   10                  15
CGT CGC CGC CAG CGG CGA GCG GCA CGG AGA CGG AGG  84  (Seq ID 7).
Arg Arg Arg Gln Arg Arg Ala Ala Arg Arg Arg Arg
                20                  25
```

Note the DNA sequences assigned Seq ID numbers 1, 3, 5, and 7 are the gene sequences containing the codons to obtain the peptides having Seq ID Nos. 2, 4, 6, and 8. The DNA fragments having Seq ID Nos 1,3,5, and 7 are regarded as novel intermediate compounds that constitute part of the present invention.

The Origin and Utility of these Four Oligonucleotides

The Oligonucleotide of Seq ID 1 is the part of the Herpes Simplex Virus Type 1 immediate early (IE) gene 3 for the transcriptional activator IE 175 (=ICP 4). Its 84 nucleotides are located from bp 3760 up to 3844 according to the known gene nucleotide sequence Herpes Simplex Virus Type 1, Viridae; DS-DNA Enveloped Viruses; Herpes Viridae, Alpha-Herpes Virinae. This same oligonucleotide may also be found in the complete short unique region 2 with partial terminal and inverted repeats in DNA, HSV 1, Strain 17.

The oligonucleotide of Seq ID 3 is the part of the Human Cytomegalovirus (Strain AD 169) complete genome (from base pair 70001 up to base 80100). Its 75 nucleotides are located from bp 2342 up to 2416 in this region of the Human Cytomegalovirus gene Strain AD=169 according to Human Cytomegalovirus, Viridae, DS-DNA Enveloped Viruses, Herpesviridae, Betaherpesvirinae.

The oligonucleotide of Seq ID 3 is in the Human Cytomegalovirus F fragment DNA encoding DNA Polymeraseycoprotein B also and has homology with DNA from the following viruses:
  (a) Epstein-Barr Virus, artifactual joining of B95-8 complete gene and the sequences from ragi of the large deletion found in B95-8 (from base pair 70001 to 80100) about 70%.
  (b) HSV1 (strain 17) complete short unique region with inverted repeat DNA, (from bp 10001 to 20100) about 65%.
  (c) HSV2 ORF1, ORF2, and ORF 3 (LAT) gene about 65%.

The oligonucleotide with Seq ID5 is the part of Herpes Simplex virus type one (HSV 1) latency associated transcript (LAT).

Its 78 nucleotides are localized from 2255 up to 2332 positions of LAT gene according to Herpes Simplex Virus Type 1, Viridae, DS-DNA Enveloped Viruses; Herpes Viridae, Alpha-Herpes-virinae.

This oligonucleotide has homology:
  with Herpes Simplex virus type 1 Bam H1 fragment B DNA sequence—about 97.5%:
  with Herpes Simplex virus type 1 gene encoding two latency—related proteins—about 97.5%;
  with Pseudorabies virus immediate—early gene—about 70%;
  with Herpes Simplex virus type 2 ORF1, ORF2, and ORF3 (LAT) gene—about 70%;
  with Epstein-Barr virus, artifactual joining of B95-8 complete genome and the sequences from raji of the large deletion found in B95-8 (from base 70001 to 80100—about 65.5%;
  with Bovine Herpesvirus type 1 early—intermediate transcription control protein (BICP4) gene—about 70%;
  with Human Cytomegalovirus UL56 gene—67.5%;

The oligonucleotide with Seq ID 7 is part of Human Cytomegalovirus (HCMV) short unique region, short repeats, and part of long repeat (from base 1 to base 10100).

Its 84 nucleotides are localized from 5340 up to 5424 positions in this part of genome according to Human Cytomegalovirus, Viridae; DS-DNA Enveloped Virules; Herpes Viridae; Betaherpesvirinae This oligonucleotide has homology:
  with Equine Herpesvirus 4 (EHV4) genome, thymidine kinase (TK) and glycoprotein H (GH) genes—about 71%
  with Herpes Simplex virus type 2 immediate—early (IE5) protein mRNA, 5' end—about 65%;
  with Herpes Simplex virus type 1 complete genome from base 70001 to base 80100—about 65.5%.

Isolation of the oligonucleotides sequences from the viral DNA that code for the four peptides indicated above.

The viral DNA is isolated from corresponding viral suspension obtained from HELC infected by Herpes Simplex 1 or Human Cytomegalovirus (see above about cell cultures and virus strains), purified by agarose gel electrophoresis (AGE) according to Myers, R. M. et al, "Detection and Localization of Single Base Changes by Denaturing Gradient Gel Electrophoresis; Methods Enzymol. 155:501 to 527 (1987) and Myers et al, "In Genome Analysis: A Practical Approach" (Ed. K. Davies) p. 95 IRL Press, Oxford (1988), treated by restriction enzymes and subjected by polyacrylamide gel electrophoresis.

The isolation of oligonucleotide with Seq ID 1 from Herpes Simplex virus type I immediate early (IE) gene 3 for transcriptional activator IE 175 (=ICP4) is produced after treating DNA by restriction enzyme NcoI with recognition sequence CGATGG. This procedure according to PAAG, EF gives the polynucleotide with 2308 pair of bases (from 2637 up to 4935 position) with the actual fragment located from 3760 up to 3844 position.

The isolation of oligonucleotide with Seq ID 3 from HCMV (strain AD169) complete genome is produced after treating of DNA by restriction enzyme Bst E III with recognition sequence GATC. This procedure after PAAG, EF gives the polynucleotide with 2182 pair of base—from 715 to 2898 position—with the actual fragment from 2342 up to 2416 position.

The isolation of oligonucleotide with Seq. ID5 from HSVI (LAT) is produced after treating of DNA by restriction enzyme Nco 1 with recognition sequence CCATGG. This procedure after PAAG, EF gives the polynucletide with 1737 pair of base—from 659 up to 2396 position—with actual fragment from 2255 up to 2332 position.

The isolation of oligonucleotide with Seq ID 7 from HCMV—short unique region, short repeats, and part of long repeat is produced after treating of DNA by restriction enzyme Nco 1 also. This procedure after PAAG, EF gives the polynucleotide with 4807 pair of base with actual fragment from 5340 up to 5424.

The structures of the Herpes Simplex Virus Type I Immediate Early (IE) Gene 3 for Transcriptional Activator IE 175; HCMV (Strain AD 169); HSVI (LAT); and HCMV—Short Unique Region are known in the art and may be found in EMBL-37.

The construction of recombinant plasmid DNA for expression of the four peptides, with Seq Nos. 2, 4, 6 and 8.

All 4 oligonucleotides are introduced into a polylinker of plasmid pRSET with sites of restriction, including Nco 1 and Bst E III. This plasmid may be used to transform *E.Coli* (AB 109 strain). For this aim bacteria are treated with $CaCl_2$ which makes their membranes slightly permeable (competent bacteria). The transformed bacteria are then selected by growing them on a medium containing ampicillin. pRSET is a commercial multicopy expressing vector with a high level of protein expression.

Chemical Synthesis

The four sequences having the formulae Seq. Nos. 2,4,6 and 8 may also be prepared by direct peptide synthesis that is well known in the art according to the syntheses employed in *The Peptides*, Schroeder and Luebke, Vol. I, Methods of Peptide Synthesis, Academic Press (1965). Preferably each of the four polypeptides having Seq Nos. 2,4,6 and 8 are synthesized starting from the amino terminal acid and forming the peptide bond between the carboxy terminal of the given amino acid and the amino terminal of the next given amino acids. This procedure is carried out until all of the amino acids needed to make each of the four peptides are formed into whole chains.

Where it is necessary to employ an amino-protecting group to protect an N-terminal amino substituent to carry out the synthesis of one or more of the four above-mentioned peptides, the approaches of pages 3 through 51 of *The Peptides* may be employed. Where it is necessary to employ a carboxy-protecting group to protect either a C-terminal carboxy group or a carboxy group forming part of a side chain (i.e. Glu, Asp) to carry out the synthesis of one or more of the four above-mentioned polypeptides, the methods of page 52 through 75 of the reference are employed.

Glycine and alanine are relatively simple amino acids common to the presently claimed peptides. Where it is necessary to block the amino terminal, carbobenzoxy groups are employed. Where it is necessary to block the carboxy terminal, a benzyl ester is formed. See pages 137 and 138 of *The Peptides*. In fact the information regarding blocking the C- and N-terminals of simple amino acids such as glycine and alanine without highly reactive side chains is still highly relevant to the blocking of all amino acids involved in the synthesis of the peptides of the present invention.

One amino acid common to all four peptides of the Seq Nos 2, 4, 6 and 8 is arginine. Arginine has a guanido group on its side chain and sometimes this group may be responsible for undesired side reactions. Pages 167 through 174 of *The Peptides* discusses peptide synthesis using a number of different blocking groups to protect the guanido side chain. Pages 175 and 176 discuss peptide synthesis involving arginine where the guanido side chain need not be blocked.

Another amino acid that is well represented among the four peptides of this invention is proline. Proline is a heterocyclic amino acid with an imino functional group. Where it is necessary to block the imino group, pages 146 through 148 of *The Peptides* provides details.

Serine is an amino acid present in three of the four new peptides. Serine contains a side chain that includes a hydroxy group. In some situations the hydroxy group may undergo undesired side reactions. *The Peptides* on pages 207 through 214 describes peptide synthesis using serine with and without protecting groups for the hydroxy group on the side chain.

Threonine is another amino acid present in three of the four new polypeptides that also contains a side chain having a hydroxy substituent. In some situations the hydroxy group may undergo undesired side reactions. *The Peptides* on pages 214 through 216 describes peptide synthesis using threonine with and without protecting groups for the hydroxy group on the side chain.

Tryptophan is an amino acid present in the new peptide of Seq. ID No. 8. Tryptophan is an indole and thus contains an indole nitrogen that can undergo undesired side reactions. Pages 148 through 150 of *The Peptides* describes peptide synthesis using tryptophan.

Glycine and alanine are relatively simple amino acids common to the presently claimed peptides. Where it is necessary to block the amino terminal, carbobenzoxy groups are employed. Where it is necessary to block the carboxy terminal, a benzyl ester is formed Where it is necessary during peptide synthesis to facilitate the reaction of the C-terminal of a given amino acid or peptide, the activated ester technique as described in *The Peptides* on pages 97 to 108 may be employed.

Solid Phase Synthesis of the Four Peptides

The synthesis of each of the four peptides with the Sequence ID Nos. 2, 4, 6 and 8 according to the instant patent application was carried out. Each of the four peptides was produced by the Automation of Solid Phase Synthesis with the following High Performance Liquid Chromatography (HPLC). See AminoTech. 1991. Biochemical and Reagents for Peptide Synthesis. AminoTech Catalogue, AminoTech, Nepean, Ontario.

The amount of the first HPLC-peptide (product 9410-147, Seq. ID No. 2) produced equalled 15 mg. The amino acid analysis of this peptide is presented in Table 1.

The amount of the second HPLC-peptide (product 9410-148, Seq. ID No. 2) produced equalled 20 mg. The amino acid analysis of this peptide is presented in Table 2.

The amount of the third HPLC-peptide (product 9410-149 Seq. ID No. 6) produced equalled 15 mg. The amino acid analysis of this peptide is presented in Table 3.

The amount of the fourth HPLC-peptide (product 9410-151 Seq. ID No. 8) produced equalled 50 mg. The amino acid analysis of this peptide is presented in Table 4.

TABLE 1

FINAL REPORT OF AMINO ACID ANALYSIS FOR SYNTHETIC PEPTIDE HAVING SEQ ID NO. 2
Date: 10-3-93
Sample: Peptide #: 9410-147

| RESIDUES | EXPECTED COMPOSITION | DETECTED COMPOSITION |
|---|---|---|
| Asp/Asn | | |
| Thr | 1 | 1.05 |
| Ser | 1 | 0.96 |
| Glu/gln | 2 | 2.08 |
| Pro | 12 | 12.48 |
| Gly | 1 | 1.05 |
| Ala | 9 | 9.4 |
| Cys | | |
| Val | | |
| Met | | |
| Ile | | |
| Leu | 1 | 0.95 |
| Tyr | | |
| Phe | | |
| His | | |
| Lys | | |
| Arg | 1 | 1.04 |
| Trp | | |

*The peptide was hydrolyzed for one hour with 6N HCl containing 0.1% phenol at 160° C.
**The composition of the peptide was analyzed on a reverse-phase HPLC column.

TABLE 2

FINAL REPORT OF AMINO ACID ANALYSIS FOR SYNTHETIC PEPTIDE HAVING SEQ ID NO. 4
Date: 10-3-94
Sample: Peptide #: 9410-148

| RESIDUES | EXPECTED COMPOSITION | DETECTED COMPOSITION |
|---|---|---|
| Asp/Asn | 1 | 0.95 |
| Thr | 1 | 1.04 |
| Ser | 1 | 1.05 |
| Glu/gln | 1 | 0.96 |
| Pro | 9 | 9.38 |
| Gly | 1 | 0.96 |
| Ala | 3 | 3.12 |
| Cys | | |
| Val | | |
| Met | | |

TABLE 2-continued

FINAL REPORT OF AMINO ACID ANALYSIS FOR SYNTHETIC
PEPTIDE HAVING SEQ ID NO. 4
Date: 10-3-94
Sample: Peptide #: 9410-148

| RESIDUES | EXPECTED COMPOSITION | DETECTED COMPOSITION |
|---|---|---|
| Ile | | |
| Leu | 5 | 4.81 |
| Tyr | | |
| Phe | | |
| His | | |
| Lys | | |
| Arg | 3 | 3.13 |
| Trp | | |

*The peptide was hydrolyzed for one hour with 6N HCl containing 0.1% phenol at 160° C.
**The composition of the peptide was analyzed on a reverse-phase HPLC column.

TABLE 3

FINAL REPORT OF AMINO ACID ANALYSIS FOR SYNTHETIC
PEPTIDE HAVING SEQ ID NO. 6
Date: 10-3-94
Sample: Peptide #: 9410-149

| RESIDUES | EXPECTED COMPOSITION | DETECTED COMPOSITION |
|---|---|---|
| Asp/Asn | 1 | 1.05 |
| Thr | 1 | 0.96 |
| Ser | 1 | 1.05 |
| Glu/gln | | |
| Pro | 3 | 2.88 |
| Gly | 15 | 15.42 |
| Ala | 3 | 1.03 |
| Cys | | |
| Val | | |
| Met | | |
| Ile | | |
| Leu | | |
| Tyr | | |
| Phe | | |
| His | | |
| Lys | | |
| Arg | 4 | 4.16 |
| Trp | | |

*The peptide was hydrolyzed for one hour with 6N HCl containing 0.1% phenol at 160° C.
**The composition of the peptide was analyzed on a reverse-phase HPLC column.

TABLE 4

FINAL REPORT OF AMINO ACID ANALYSIS FOR SYNTHETIC
PEPTIDE HAVING SEQ ID NO. 8
Date: 10-3-94
Sample: Peptide #: 9410-150

| RESIDUES | EXPECTED COMPOSITION | DETECTED COMPOSITION |
|---|---|---|
| Asp/Asn | | |
| Thr | | |
| Ser | | |
| Glu/gln | 1 | 1.04 |
| Pro | | |
| Gly | 4 | 4.18 |
| Ala | 4 | 3.84 |
| Cys | | |
| Val | | |
| Met | | |
| Ile | | |
| Leu | | |
| Tyr | | |
| Phe | | |
| His | | |
| Lys | | |
| Arg | 18 | 18.66 |
| Trp | 1 | 1.05 |

*The peptide was hydrolyzed for one hour with 6N HCl containing 0.1% phenol at 160° C.
**The composition of the peptide was analyzed on a reverse-phase HPLC column.

Determination of Immunogenic Activity of the Peptide Vaccine

1. Coupling Peptides to Protein Carriers With Glutaraldehyde

Glutaraldehyde is a bifunctional coupling agent that couples amino groups on the peptide to amino groups on the protein carrier Keyhole Limpet Hemocyanin (KLH). For preparing each complex of peptide-KLH with glutaraldehyde, it was necessary to carry out the following procedures:

(1) 20 mM glutaraldehyde were prepared;

(2) KLH was dissolved in water;

(3) Each of the four peptides was added to the water individually;

(4) The glutaraldehyde was added dropwise with stirring to the water over the course of 5 minutes at room temperature. Stirring of the solution was continued for another 30 minutes. The solution became yellow.

(5) Glycine was then added to the solution to block any unreacted glutaraldehyde and allowed to remain for 30 minutes;

(6) Excess peptide and reagent were then removed by either exhaustive dialysis in phosphate-buffered saline (see Kagan & Glick 1979. "Oxyitocin", Methods of Hormone Radioimmunoassay. B. B. Jaffe & H. R. Behrman, eds. pp 328 to 329, Academic Press, NY).

2. Immunization of Rabbits on the Basis of a Special Schedule of Injections by a Mixture of Equal Amounts of All Peptides For the study to determine the immunogenic activity of the four peptides, a mixture of equal amounts of all four of the peptides with Seq. ID numbers 2, 4, 6 and 8 with KLH was used. Immunization of two rabbits (designated R76 and R77) was carried out according to the following immunization schedule:

(a) first bleeding;

(b) day 1, first injection;

(c) day 8, second injection;

(d) day 24, third injection;

(e) day 40, fourth injection;

(f) day 55, fifth injection;

(g) from 70th day, second and final bleeding

The immunization dose was 0.5 mg per injection.

3. ELISA Titration of Rabbit's Immunosera with Synthetic Peptides

In the present case for the measurement of antibodies in rabbit sera, each of the four peptide reagents (which are the same four peptides that are the active ingredients in the vaccine) was fixed to a specific plastic microplate, incubated with each test serum (from Rabbit R76 or R77) (obtained both before and after administering the vaccine) at dilutions of 1:30,000, 1:10,000: 1:3,000 and 1:1,000), washed, and then reinoculated with an anti-immunoglobulin labelled with an enzyme, namely, horseradish peroxidase.

The enzyme activities were measured by adding the substrate for the enzyme and estimating the color reaction in a spectrophotometer. The amount of antibody bound to the absorbed peptide reagents is proportional to the enzyme activity. Once the substrate for the enzyme is added the enzymatic activity is determined and the amount of unknown antibody is determined as a function of the measured enzyme activity.

The ELISA was carried out using the following steps:

1. A 96-well plate was coated with 20 ug/ml of free peptide in 0.01M sodium phosphate buffer, pH 7.2 containing 0.1M NaCl (PBS) (50 ul/well, 4 overnight),
2. The plate was washed twice with PBS and block the wells with TANA'S$^R$ blocking solution for one hour at 37° C.,
3. The wells were incubated with diluted serum (using 1.0% BSA/PBS for dilution, 37° C. for 2–4 hours),
4. Each well was washed four times with PBS, and then incubated with 1:3,000 diluted goat antirabbit IgG-horseradish peroxidase conjugate (TANA Lab., using 1.0% BSA/PBS for dilution) for 1 hour.
5. Each well was washed four times with PBS, and then incubated with TANA's$^R$ calorimetric ELISA substrate (tetra methylbenzene/H202 solution),
6. The enzyme reaction was stopped with TANA's$^R$ ELISA-stopping buffer (diluted phosphoric acid),
7. The plates were read using 450 nm.

Figure 1:
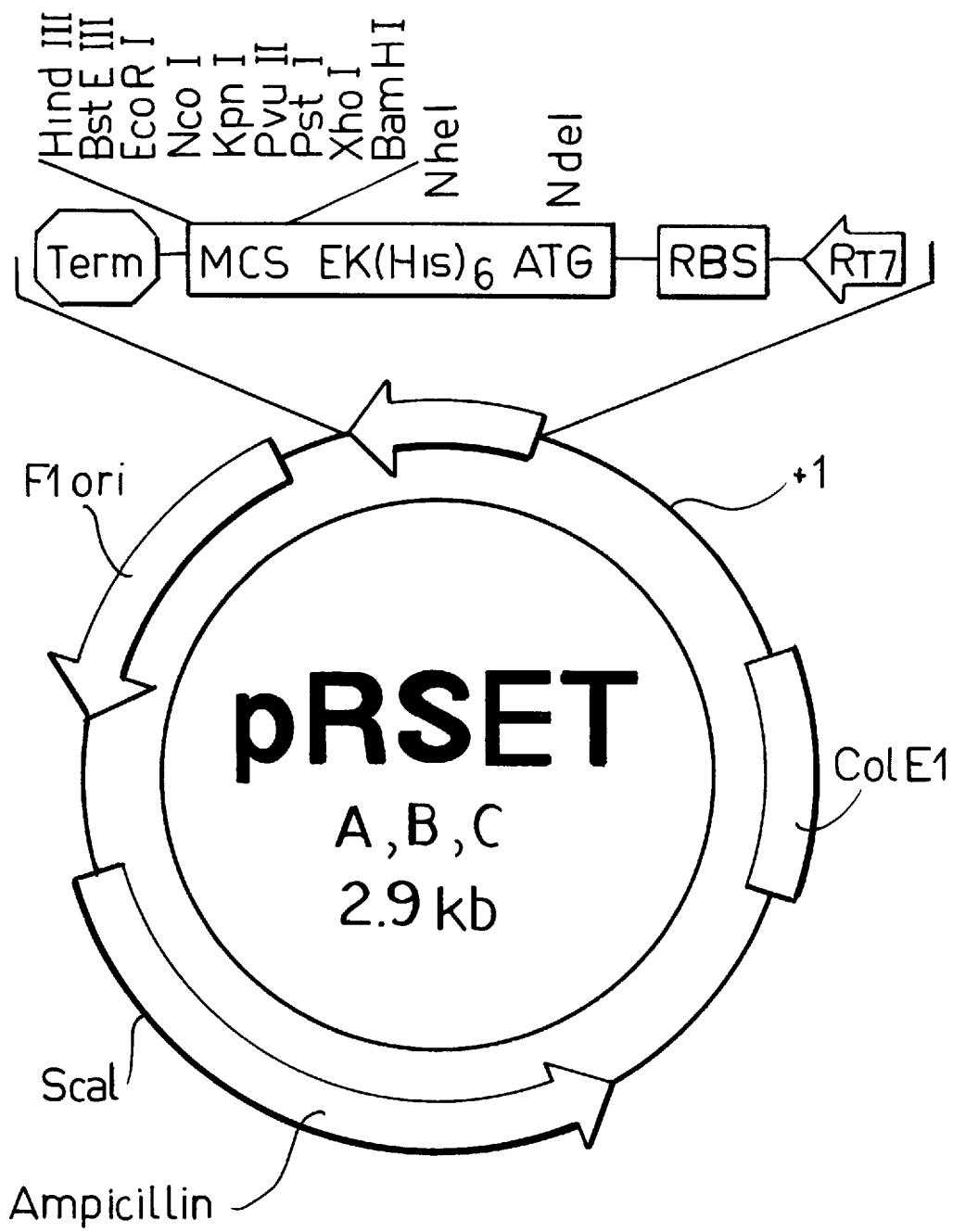
FIG. 1 is a map of the expression vector plasmid PRSET (prior art).
Figure 2:
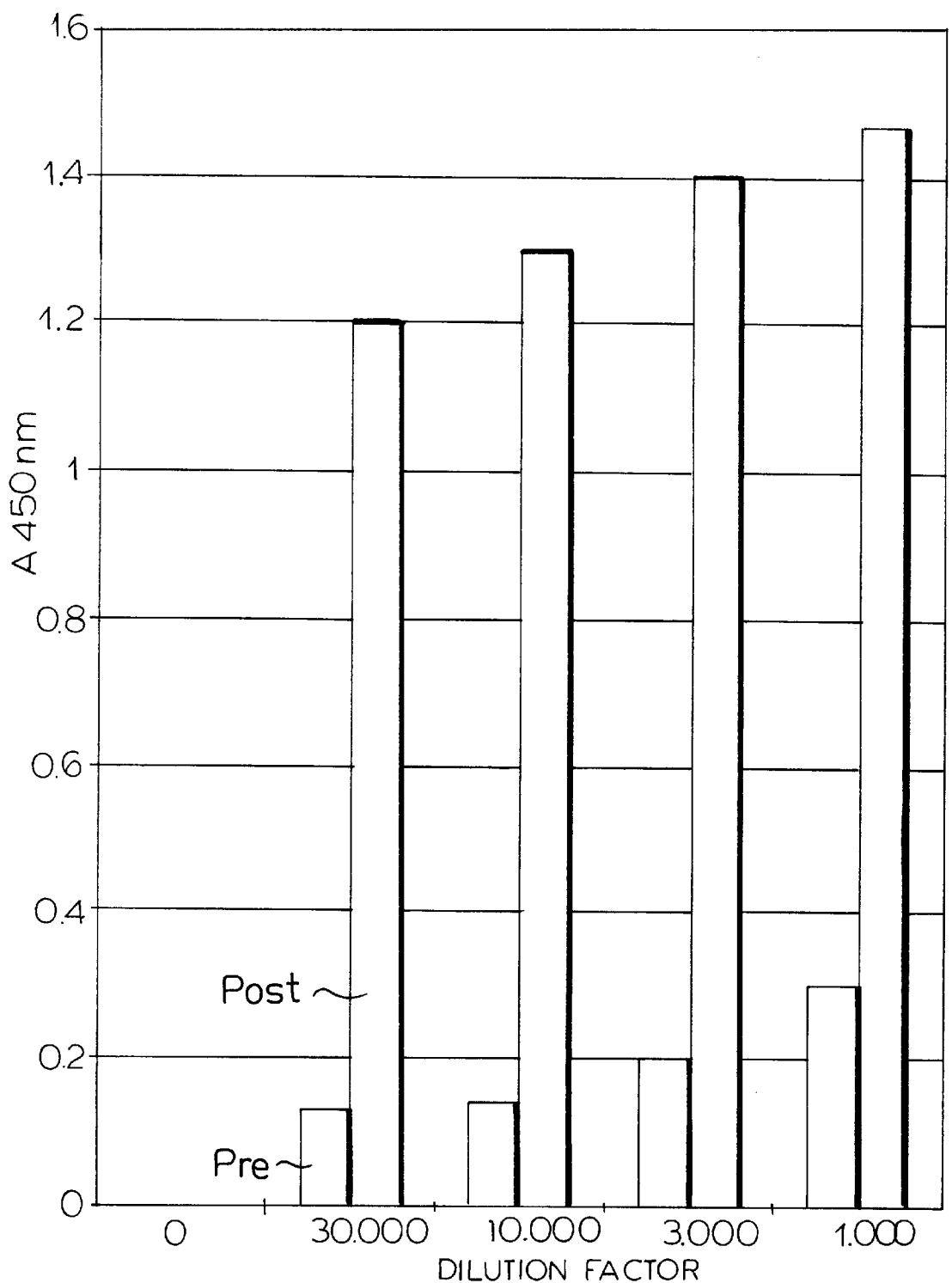
FIGS. 2 and 3 are series of bar graphs showing the results of an enzyme-linked immunosorbent assay (ELISA) on rabbit sera #76 and #77 obtained from rabbits before and after immunization with the present peptide-containing vaccine using the peptide having Sequence ID #2 to bind the antibodies in the sera to determine antibody formation.

On the base of this technique these data were obtained:

FIG. 2. Binding of rabbit #76 serum to first peptide with Seq. ID No. 2.

Figure 3:
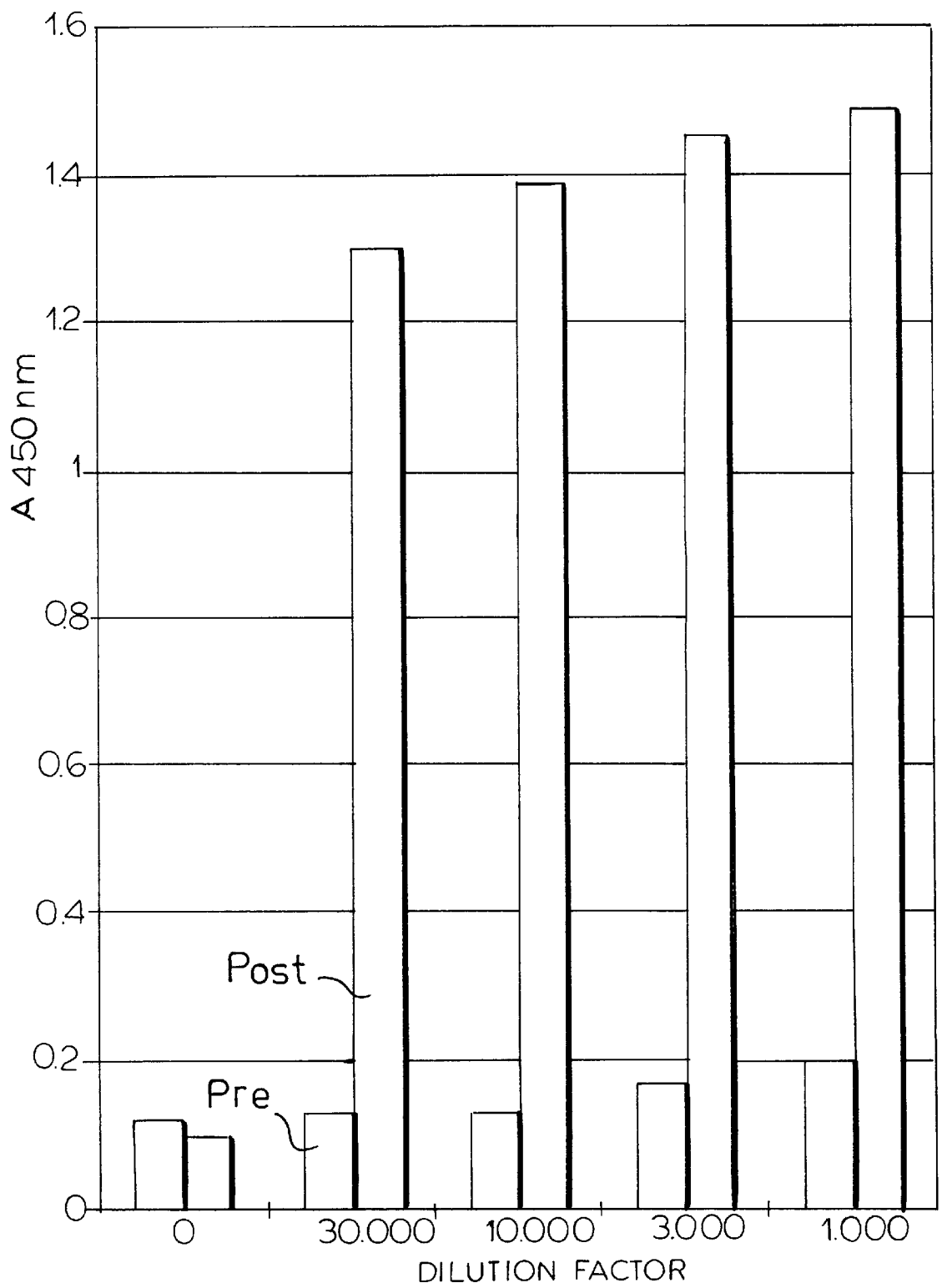

FIG. 3. Binding of rabbit #77 serum to first peptide with Seq. ID No. 2.

Figure 4:
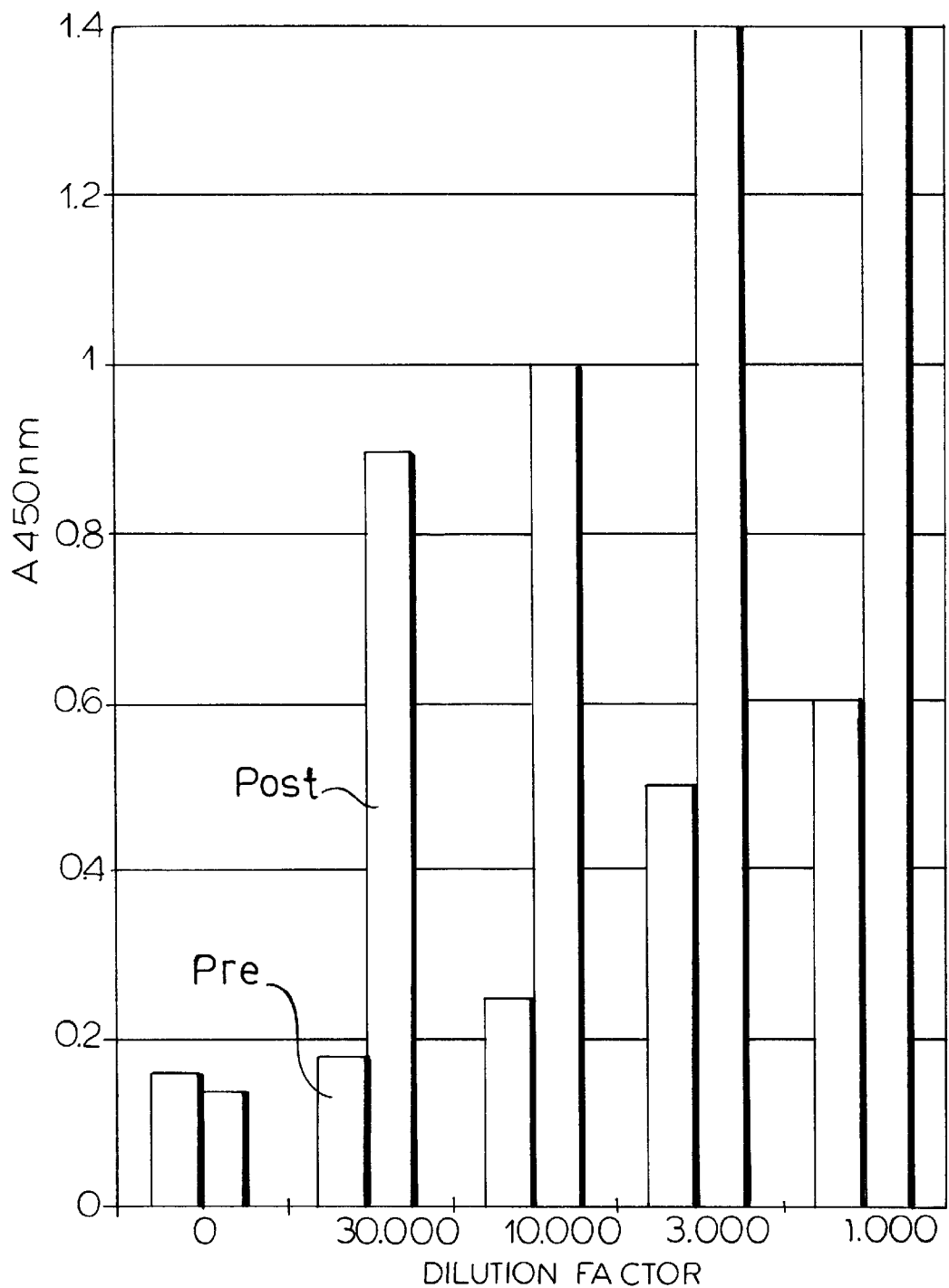
FIGS. 4 and 5 are series of bar graphs showing the results of an enzyme-linked immunosorbent assay (ELISA) on rabbit sera #76 and #77 obtained from rabbits before and after immunization with the present peptide-containing vaccine using the peptide having Sequence ID #4 to bind the antibodies in the sera to determine antibody formation.

FIG. 4. Binding of rabbit #76 serum to second peptide with Seq. ID No. 4.

Figure 5:
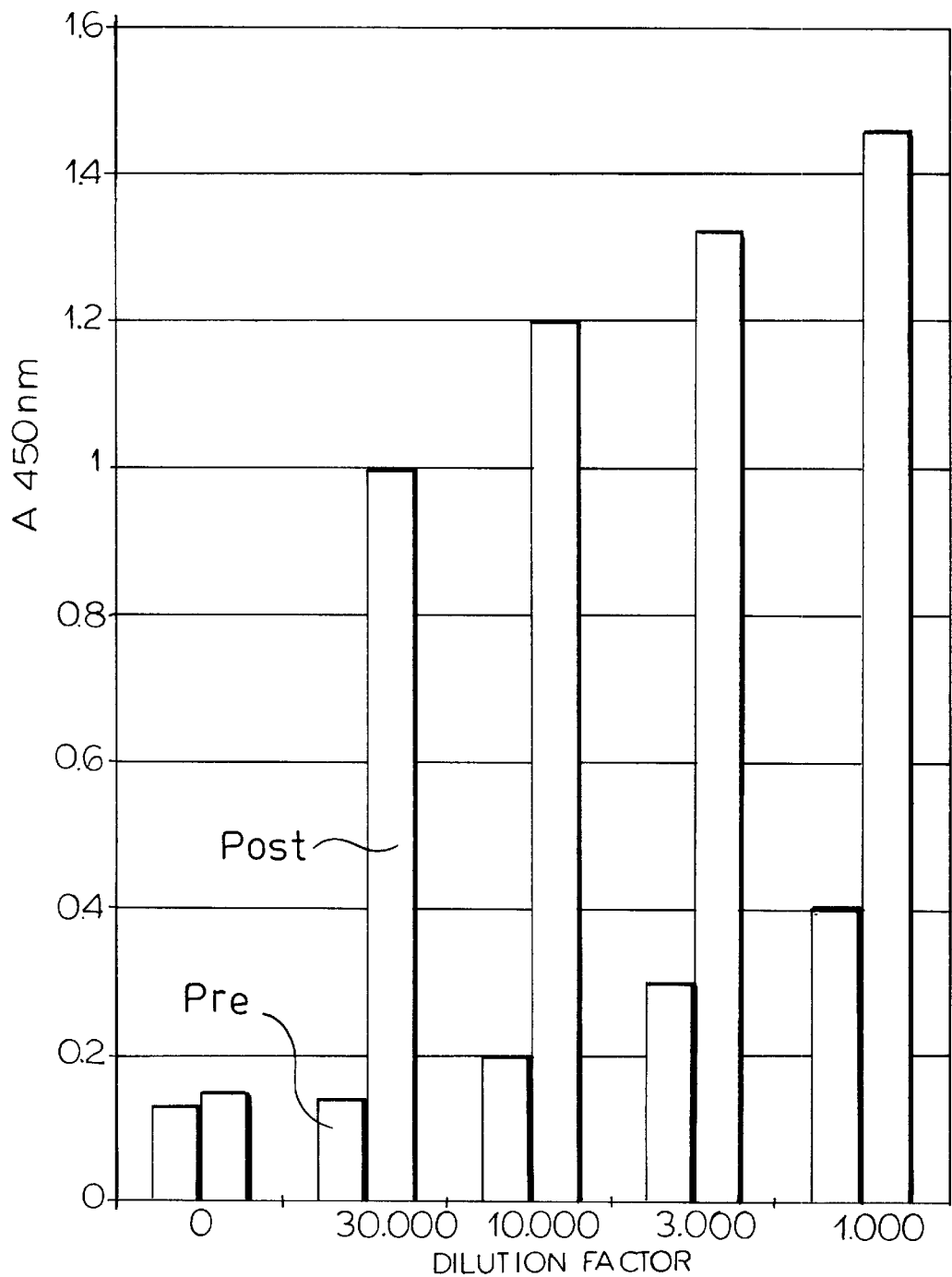

FIG. 5. Binding of rabbit #77 serum to second peptide with Seq. ID No. 4.

Figure 6:
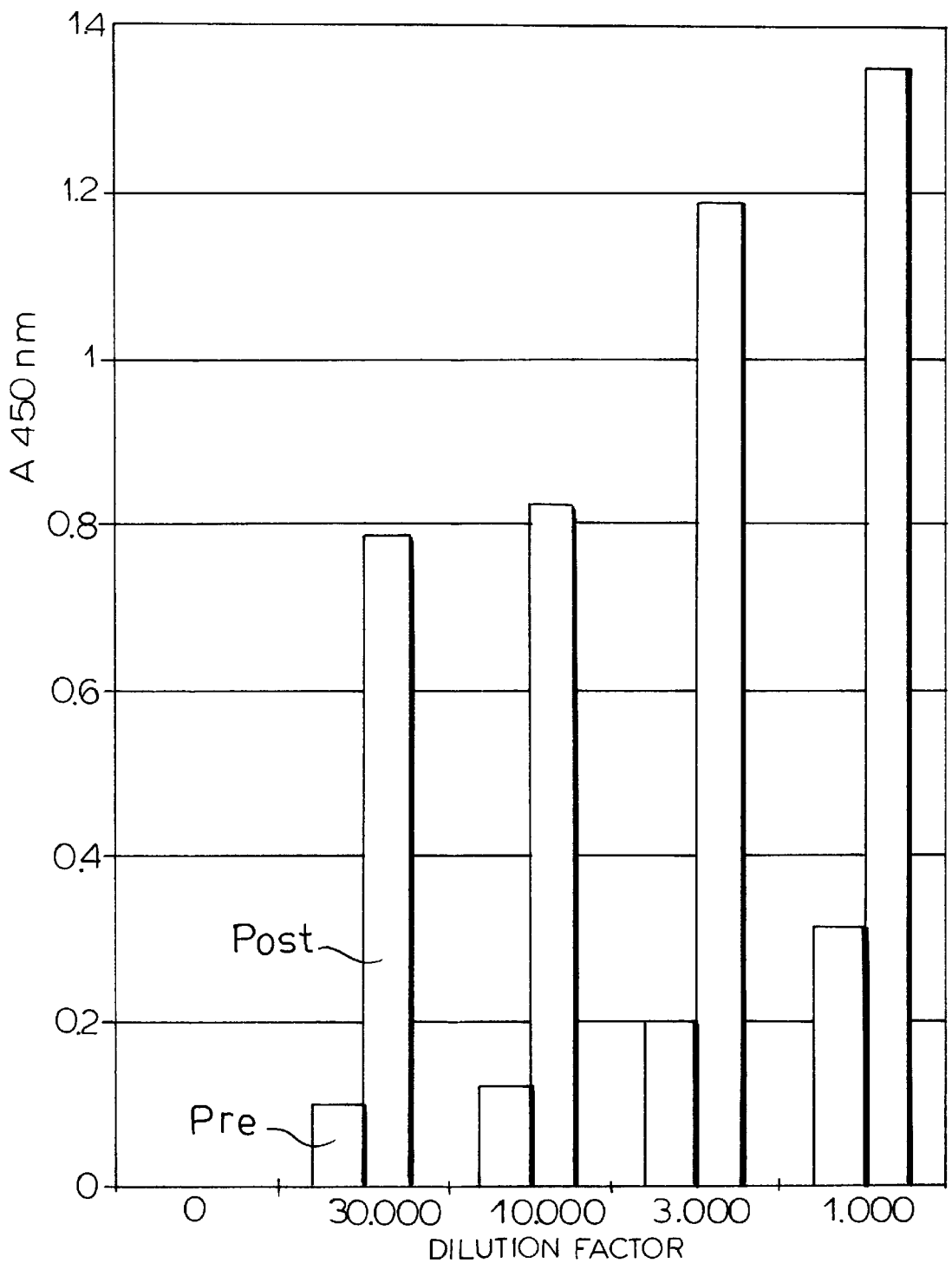
FIGS. 6 and 7 are series of bar graphs showing the results of an enzyme-linked immunosorbent assay (ELISA) on rabbit sera #76 and #77 obtained from rabbits before and after immunization with the present peptide-containing vaccine using the peptide having Sequence ID #6 to bind the antibodies in the sera to determine antibody formation.

FIG. 6. Binding of rabbit #76 serum to third peptide with Seq. ID No. 6.

Figure 7:
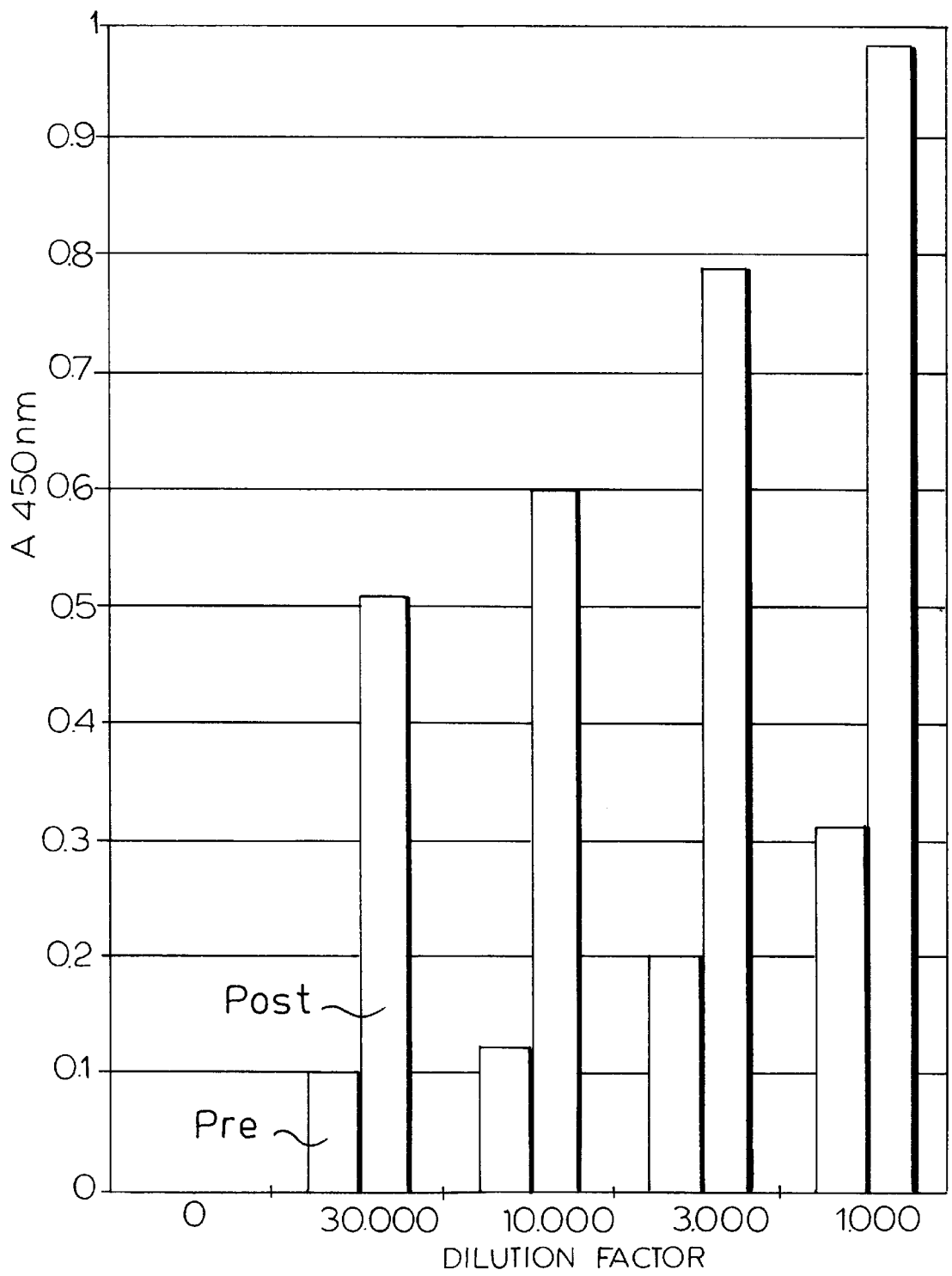

FIG. 7. Binding of rabbit #77 serum to third peptide with Seq. ID No. 6.

Figure 8:
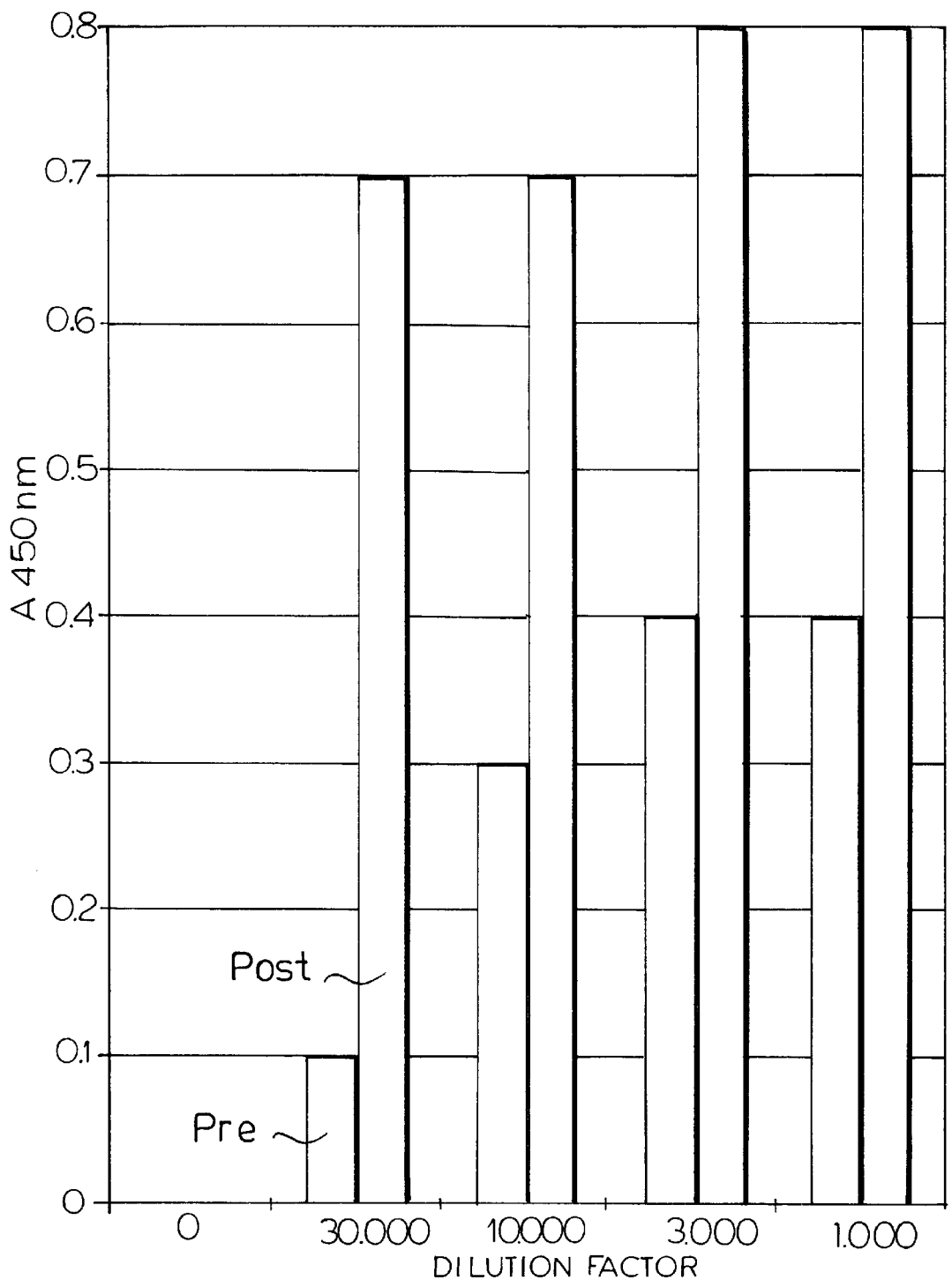
FIGS. 8 and 9 are series of bar graphs showing the results of an enzyme-linked immunosorbent assay (ELISA) on rabbit sera #76 and #77 obtained from rabbits before and after immunization with the present peptide-containing vaccine using the peptide having Sequence ID #8 to bind the antibodies in the sera to determine antibody formation.

FIG. 8. Binding of rabbit #76 serum to fourth peptide with Seq. ID No. 8.

Figure 9:
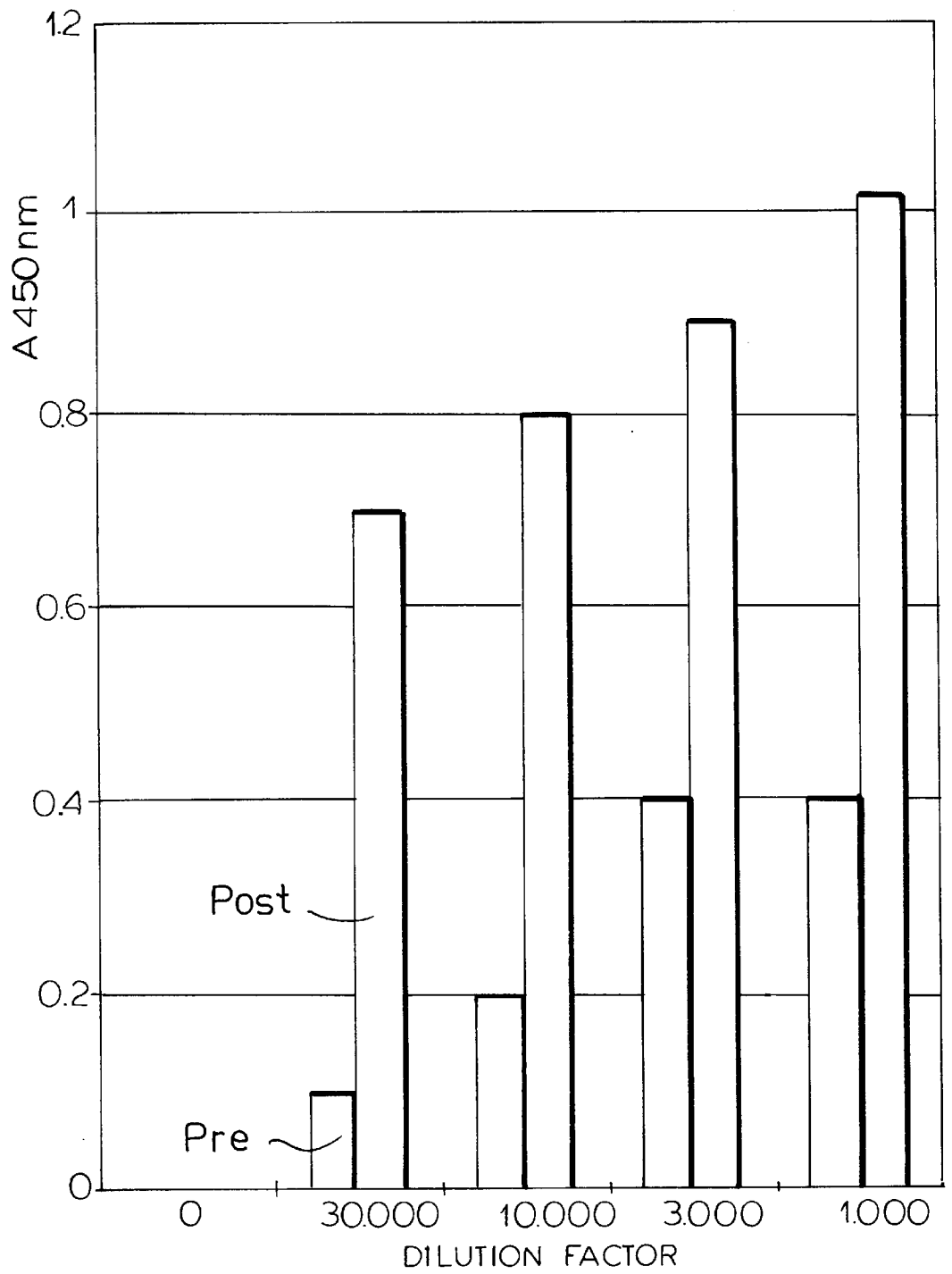

FIG. 9. Binding of rabbit #77 serum to fourth peptide with Seq. ID No. 8.

In both rabbit sera (R76 and R77) the high levels of antibodies against each of our four peptides were determined in contrast with these sera before immunization.

On the basis of ELISA titrations, it was found that two rabbits produced high titer antibodies against each of the four tested peptide reagents with Seq. ID No. 2, 4, 6 and 8. The results are presented in FIGS. 2 through 9. Note the large difference in the immunogenic activity in the rabbit blood before and after the peptide-containing vaccine was administered to the rabbits.

In two of such sera from immunized rabbit N76 (R76) and immunized rabbit N77 (R77) and in pre-immune (normal) sera (R78) in the Laboratory of Microbiological Associates, Inc. (MA) the level (titers) of antibodies were determined against:

Herpes Simplex Virus 1 (HSV1)—on the basis of MA'sELISA

Herpes Simplex Virus 2 (HSV2)—on the basis of Whittaker kit, ELISA,

Human Cytomegalovirus (HCMV)—on the basis of Whittaker kit, ELISA,

Varicella Zoster Virus (VZV) on the basis of MA's IFA,

Epstein—Bar Virus (EBV)—on the basis of MA's IFA.

Titers were determined by comparison with the mean+ 99% confidence interval for control (normal, pre-immune) serum R78 (See: Tables 5 through 8).

As one can see, strong differential reactivity was obtained for:

R76—against HSV-1+HSV-2 and HCKV,

R77—against HSV-1+HSV-2 and HCMV.

Neither antibody showed reactivity against EBV (VCA) antigen.

Although reactivity against VZV was relatively strong for R76 and R77, the R78 titer was also elevated and, therefore, did not allow low titered differential results.

Tables 5, 6, 7 and 8 showing the 95% and 99% confidence intervals for R78 titration in each assay follow hereinbelow:

TABLE 5

STUDY - HSV1
BASELINE COMPARISONS FOR CONTROL 78
CONFIDENCE INTERVALS (POOLED)

| Var Name | MEAN | STD ERR | LOWER 95% | UPPER 95% | LOWER 99% | UPPER 99% |
|---|---|---|---|---|---|---|
| 10 | 0.156 | 0.073 | −0.022 | 0.333 | −0.114 | 0.425 |
| 20 | 0.224 | 0.073 | 0.046 | 0.401 | −0.046 | 0.493 |
| 40 | 0.166 | 0.073 | −0.012 | 0.343 | −0.104 | 0.435 |
| 80 | 0.15 | 0.073 | −0.028 | 0.328 | −0.119 | 0.419 |
| 160 | 0.193 | 0.073 | 0.015 | 0.37 | −0.077 | 0.462 |
| 320 | 0.11 | 0.073 | −0.068 | 0.287 | −0.16 | 0.379 |
| 640 | 0.104 | 0.073 | −0.074 | 0.282 | −0.165 | 0.373 |
| 1280 | 0.128 | 0.073 | −0.05 | 0.306 | −0.141 | 0.397 |

TABLE 6

STUDY - HSV2
BASELINE COMPARISONS FOR CONTROL R78
CONFIDENCE INTERVALS (POOLED)

| VAR NAME | MEAN | STD ERR | LOWER 95% | UPPER 95% | LOWER 99% | UPPER 99% |
|---|---|---|---|---|---|---|
| 10 | 1.153 | 0.041 | 1.053 | 1.252 | 1.001 | 1.304 |
| 20 | 0.657 | 0.041 | 0.557 | 0.756 | 0.505 | 0.808 |
| 40 | 0.534 | 0.041 | 0.434 | 0.634 | 0.383 | 0.685 |
| 80 | 0.304 | 0.041 | 0.204 | 0.404 | 0.153 | 0.455 |
| 160 | 0.226 | 0.041 | 0.126 | 0.326 | 0.075 | 0.377 |
| 320 | 0.181 | 0.041 | 0.081 | 0.28 | 0.029 | 0.332 |
| 640 | 0.15 | 0.041 | 0.05 | 0.249 | −0.002 | 0.301 |
| 1280 | 0.13 | 0.041 | 0.03 | 0.23 | 0.021 | 0.281 |

TABLE 7

STUDY - HCMV
BASELINE COMPARISONS FOR CONTROL R78
CONFIDENCE INTERVALS (POOLED)

| VAR NAME | MEAN | STD ERR | LOWER 95% | UPPER 95% | LOWER 99% | UPPER 99% |
|---|---|---|---|---|---|---|
| 10 | 0.929 | 0.049 | 0.809 | 1.048 | 0.747 | 1.11 |
| 20 | 0.561 | 0.049 | 0.441 | 0.68 | 0.379 | 0.742 |
| 40 | 0.368 | 0.049 | 0.248 | 0.487 | 0.186 | 0.549 |
| 80 | 0.261 | 0.049 | 0.141 | 0.381 | 0.08 | 0.442 |
| 160 | 0.171 | 0.049 | 0.051 | 0.29 | −0.011 | 0.352 |
| 320 | 0.124 | 0.049 | 0.004 | 0.244 | −0.057 | 0.305 |
| 640 | 0.102 | 0.049 | −0.018 | 0.221 | −0.08 | 0.283 |
| 1280 | 0.104 | 0.049 | −0.015 | 0.224 | −0.077 | 0.286 |

TABLE 8

STUDY - VZV
BASELINE COMPARISONS FOR CONTROL R78
CONFIDENCE INTERVALS (POOLED)

| VAR NAME | MEAN | STD ERR | LOWER 95% | UPPER 95% | LOWER 99% | UPPER 99% |
|---|---|---|---|---|---|---|
| 10 | 1.364 | 0.155 | 0.966 | 1.762 | 0.74 | 1.988 |
| 20 | 1.077 | 0.155 | 0.679 | 1.474 | 0.453 | 1.7 |
| 40 | 1.069 | 0.155 | 0.671 | 1.467 | 0.445 | 1.693 |
| 80 | 0.632 | 0.155 | 0.234 | 1.029 | 0.008 | 1.255 |
| 160 | 0.44 | 0.155 | 0.042 | 0.837 | −0.184 | 1.063 |
| 320 | 0.454 | 0.155 | 0.056 | 0.851 | −0.17 | 1.077 |
| 640 | 0.145 | 0.155 | −0.253 | 0.543 | −0.479 | 0.769 |
| 1280 | 0.529 | 0.219 | −0.033 | 1.091 | −0.353 | 1.411 |

TABLE 9

The immunogenisity of each herpetic peptide and its mixtures as a result of ELISA-titration of immune rabbit sera with several members of Herpesvirus family.

| Ser/Vir | HSV1 | HSV2 | HSV1 + 2 | HCMV | EBV | VZV | MDV |
|---|---|---|---|---|---|---|---|
| Anti-P1 | 3000 | 3000 | 0 | 10000 | 10000 | 10000 | 3000 |
| Anti-P2 | 0 | 0 | 0 | 1000 | 0 | 3000 | 3000 |
| Anti-P3 | 3000 | 3000 | 1000 | 3000 | 10000 | 3000 | 3000 |
| Anti-P4 | 3000 | 3000 | 1000 | 3000 | 10000 | 3000 | 10000 |
| Anti-P5 | 0 | 0 | 0 | 0 | 3000 | 0 | 0 |
| Anti-4P | 3000 | 3000 | 0 | 1000 | 10000 | 3000 | 10000 |
| Anti-5P | 0 | 0 | 0 | 1000 | 0 | 0 | 3000 |
| Contr.ser | 0 | 0 | 0 | 0 | 0 | 0 | 0 |

At present we are providing some additional data concerning the antibody titers in sera of rabbits who have been immunized with the polypeptide vaccine according to the present invention.

After immunization of the rabbits by the polypeptide vaccine containing the four polypeptides we have obtained the next level of specific antibodies against the different herpes viruses in an ELISA test:

| | |
|---|---|
| against Herpes Simplex Virus I | 1:3000 |
| against Herpes Simplex Virus II | 1:3000 |
| against Human Cytomegalovirus | 1:1000 |
| against Epstein-Barr Virus | 1:10,000 |
| against Varicella-Zoster Virus | 1:3,000 |
| against Marek's Disease Virus | 1:10,000. |

In these experiments we have used the homogenates of cell cultures infected by several herpes viruses (from American Cell Culture Collection) as antigens for ELISA titration.

Thus, the data demonstrate that "antibody titers increase not only over control after multiple injections of the pharmaceutical composition . . . " but also possess the real protective activity of these sera against all actual members of the Herpes Viridae family.

The data presented above show that the new vaccine according to the present invention displays a real immunogenic activity, and a protective activity and this activity shows the effectiveness of the new peptide—containing vaccine to stimulate herpes antibody production against all herpes viruses. The vaccine may be designated as a polyvalent or universal herpes vaccine

EFFICACY OF THE PEPTIDE-CONTAINING VACCINE TO PREVENT THE DEVELOPMENT OF ATHEROSCLEROTIC PLAQUE

Background Information

It is known in the art that an increase of G proteins in the blood (Gs proteins) that stimulate the production of cyclic AMP prevents the development of atherosclerotic plaque. The new vaccine containing the polypeptides with Seq. ID Nos. 2, 4, 6 and 8 prevents the development of atherosclerotic plaque by stimulating the production of Gs proteins.

Atherogenesis is a consequence of persistent herpes virus infection development in blood vessel walls. In the course of this development, synthesis of a considerable number of virus-specified regulator proteins (transcriptional factors) takes place in the vessel walls. Some of these regulator proteins repress viral DNA replication and transcription, thus preventing a chronic herpes viral infection from becoming an acute infection. Owing to the homology between certain sections of the alpha subunit of the Gs protein gene and those of the genes of a number of herpes viruses, individual virus-specific transcription factors bind with GGC-GGC-GGC sections in the alpha subunit of the Gs protein gene and suppress the transcription of this gene. This in turn, decreases translation and synthesis of the Gs protein. A decrease in Gs protein production reduces cyclic AMP formation. This causes a reduction of the synthesis of cholesterol ether hydrolase, which in turn increases atherogenesis.

The antibodies generated in the rabbit in response to the injection of our polypeptide vaccine bind with one of the transcription factors described above, this factor being related to the GGC-GGC-GGC sites in the Gs protein gene. These antibodies prevent the emergence of a complex between the Gs protein gene site and the abovementioned transcription factor. The antibodies prevent the inhibitory influence of the persistent herpes virus infection on the synthesis of Gs proteins, thus mitigating the extent of atherogenesis.

Experimental Section

The prevention of the formation of the DNA-protein complex containing DNA from the Gs protein gene and protein from the herpes transcription factor by means of the antibodies generated by administration of our peptide vaccine to rabbits is illustrated with the results of the model experiments described below.

The study of DNA-protein interaction has been conducted by the shift-mobility assay method.

Shift Mobility Assay

A1. Extraction of Alpha-Protein from Nuclei

Purified nuclei from normal blood vessel endothelium and blood vessel endothelium with atherosclerotic plaques (ASP) were extracted with 0.35M NaCl. Purified nuclei were pelleted by low-speed centrifugation and re-suspended by vortexing to a final DNA concentration of 0.4 mg/ml in 0.35M NaCl, 5 mM Na-EDTA, 10 mM 2-mercaptoethanol, 10 mM Tris-HCl (pH 7.5) containing the five proteinase inhibitors (Phenylmethylsulfonyl fluoride (PMSF), antipain, leupeptin, chymostatin, and pepstatin A) at the concentration used in the nuclei isolation. After 30 minutes at 30° C. with occasional vortexing, the suspension was centrifuged at 10,000×g for 15 minutes. The supernatant containing the alpha-protein was used either immediately or after storage at −70° C. in the presence of 15% glycerol.

These alpha-proteins are new factors of herpes virus transcription and are different from the heretofore known factors of herpes virus transcription such as Sp11, Erg1, Wt1 and others. The new transcriptional factors have the ability to make the stable DNA-protein complex in vitro in the experimental model system (as described hereinbelow) and in the human organism as well as with a specific site on the alpha-subunit of the Gs proteins.

A2. Preparation of DNA-Fragments with GGC-Sites from the Promoter Region of Mouse Ribosome Protein Gene Fragments containing GGC sites were isolated from the promoter region of mouse ribosome protein gene following complete digestion of purified mouse DNA with either Hind III or Mbo II restriction enzymes. The fragments were purified separately by preparative electrophoresis in 6% polyacrylamide eluted from the gels, and thereafter separately end-labeled with 32P by T4 polynucleotide kinase and gamma-32P-ATP, following a treatment with bacterial alkaline phosphatase (Maxam and Gilbert, 1980). The labelled DNA was purified by extractions with chloroform:isopropanol (24:1 by weight) in the presence of 1% SDS, 1M NaCl and ethanol-precipitated in the presence of 10 mg/ml of linear polyacrylamide as a carrier. Equal amounts of the 32P-counts of the Hind III and MboII produced fragments of DNA were then mixed together to yield the final DNA sample with the GGC-GGC-GGC sites.

A3. Detection of the DNA-Protein Interactions by the Shift Mobility Assay

Figure 10:
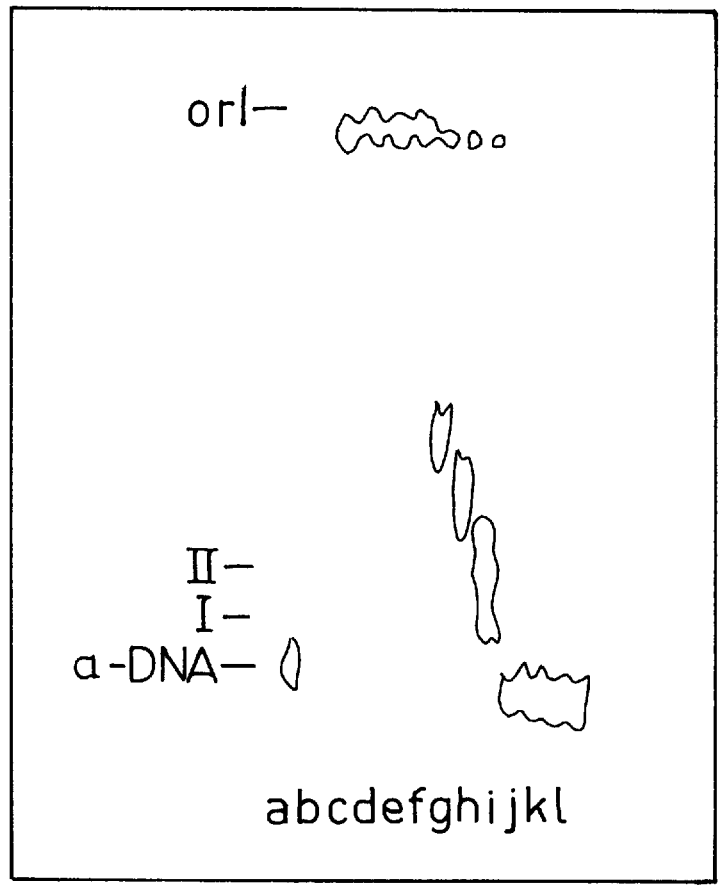
FIG. 10 is a comparative electrophoretic motility study (in 4% acrylamide gel) of the "DNA-GGC-sites-fragments" per se, with alpha-proteins of nuclei from human blood vessel endothelium (with and without ASP) and with rabbit sera (with and without antibodies against a mixture of several herpes virus peptides).

The "DNA-Protein" interactions were investigated by the Shift-Mobility Assay on a low ionic strength 4% polyacrylamdide gel (See FIG. 10).

As it is shown, pure DNA-fragment DNA (see A2) in the absence of any addition of protein extract, migrates in the gel in a discrete band. See FIG. 10, Lane "a", while in the presence of protein extract (extracted from the purified nuclei of blood vessel endothelium with ASP), most of the DNA failed to enter the gel. See FIG. 10, Lanes "b" and "c". The same result was shown with a mixture of "DNA" plus "ASP" plus rabbit sera where the rabbit sera did not contain the antibodies against the herpes peptides generated by the rabbit upon administration of the polypaptide vaccine. See FIG. 10, Lanes "d" and "e".

In the presence of an aliquot of extracts of purified nuclei of human blood endothelum without ASP (normal endothelium "NE") the "DNA" migrated to an intermediate extent. See Lanes "f" and "g" of FIG. 10.

In the presence of "ASP" and rabbit immune sera ("IS") in dilution 1:50 to 1:10 "DNA" migrates as a discrete band as pure DNA (see FIG. 10, Lanes "i" through "1" and compare with the results in Lane "a", which shows pure "DNA" without protein or immune sera). In the case of the addition to the complex of "DNA" plus "ASP" the "IS" in dilution 1:100 and 1:50, the "DNA" migrates to an intermediate extent. See FIG. 10, Lane "h"

Further analysis of the shift mobility assay as shown in FIG. 10 is as follows:

FIG. 10 shows the electrophoretic mobility in 4& polyacrylamide gel of the "DNA-GGC sites fragments", with alpha proteins of nuclei from human blood vessel endothelium (with and without ASP) and with rabbit sera (with and without antibodies generated by administration of the present polypeptide vaccine to rabbits).

Lane "a" "DNA-GGC fragment" (25,000 cpm, 2.5 ng of DNA) in the absence of added protein extract and any sera.

Lanes "b" through "e" "DNA-GGC site fragments" in the same concentration+aliquot of the extracts of purified nuclei from human blood vessel endothelium cells with ASP (b,c) and+aliquot of the normal (pre-immune) rabbit sera—N76 (d) and N77(e) in dilution 1:2.

Lanes "f" and "g" "DNA-GGC- sites fragments" in the same concentration+aliquot of the extracts of purified nuclei from normal human blood vessel endothelial cells without ASP.

Lane "h" "DNA-GGC sites fragment" in the same concentration+a mixture of aliquots of the extract of purified nuclei from endothelial blood vessel cells with ASP+aliquot of the mixture of the post-immune rabbit sera N76 and N77 in a dilution of 1:100.

Lanes "I" through "l" are the same situation as in Lane "h", but the mixture of immune sera was used in a dilution of 1:50(I); 1:30(j); 1:20(k); and 1:10(1).

These data show that the usage of immune rabbit sera against several herpesvirus peptides can prevent formation of the complex between DNA GGC-GGC-GGC binding sites on the mouse ribosomal protein gene which shares this binding site in common with the genes expressing the Gs proteins and the protein extract from the nuclei of blood vessel endothelium with "ASP" and consequently prevents the development of "ASP".

In the experiment presented above the antibodies in the immune rabbit sera decrease the formation of the DNA-protein complex by more than 90% according to the data in FIG. 10 and that such a decrease in the formation of the complex will facilitate the in vivo expression of the Gs protein genes to produce Gs proteins which in turn leads to increased cyclic AMP production and less formation of atherosclerotic plaque (ASP);

We performed an additional experiment using gel retardation to analyze the mobility of the "DNA-GGC sites fragment" in 5% PAAG. The results are shown in FIG. 11.

According to FIG. 11, the immunosera number 77 (N4) and number 76 (N6) (with dilution 1:20) had decreased the formation (amount) of DNA-protein complex between DNA-GGC-fragment labelled by 32P and the alpha-protein nuclei from human blood vessel cells with ASP in comparison with the amount of the DNA-protein complex when the corresponding pre-immune sera N5 and N7 were employed instead.

Both of the immune sera N1 and N2 as well as the preimmune sera 76 (N3) had no influence on the formation (amount) of the DNA-protein complex, when such sera were used in a dilution of 1:100.

These additional data confirm that the use of immune rabbit sera containing antibodies generated by administration of the present peptide vaccine, can prevent the formation of a DNA-protein complex between DNA-GGC site fragments characteristic of the gene that expresses the Gs proteins and protein extract the nuclei of blood vessel endothelium with ASP, characteristic of the herpes transcriptional factor, and consequently the polypeptide vaccine can prevent the development of ASP.

What is claimed is:

1. A composition for generating an immune response to a herpes infection which consists essentially of:
   (a) 10 to 30% of a peptide having Sequence ID 2;
   (b) 10 to 30% of a peptide having Sequence ID 4;
   (c) 10 to 30% of a peptide having Sequence ID 6; and
   (d) 10 to 30% of a peptide having Sequence ID 8 all in combination with a pharmaceutically acceptable inert carrier.

2. A method of generating an immune response to a herpes infection which comprises the step of administering to a mammalian subject an effective amount of a composition consisting essentially of:
   (a) 10 to 30% of a peptide having Sequence ID 2;
   (b) 10 to 30% of a peptide having Sequence ID 4;
   (c) 10 to 30% of a peptide having Sequence ID 6; and
   (d) 10 to 30% of a peptide having Sequence ID 8.

3. The method of generating an immune response to a herpes infection as defined in claim 2 wherein the composition is administered to the mammalian subject by injection.

* * * * *